(12) United States Patent
Bicek et al.

(10) Patent No.: US 6,579,297 B2
(45) Date of Patent: Jun. 17, 2003

(54) STENT DELIVERY SYSTEM USING SHAPE MEMORY RETRACTION

(75) Inventors: Andrew D. Bicek, Big Lake, MN (US); Lance A. Monroe, New Hope, MN (US); Anthony C. Vrba, Maple Grove, MN (US); Steven E. Walak, Natick, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 107 days.

(21) Appl. No.: 09/818,202

(22) Filed: Mar. 27, 2001

(65) Prior Publication Data

US 2001/0012944 A1 Aug. 9, 2001

Related U.S. Application Data

(60) Division of application No. 09/283,444, filed on Apr. 1, 1999, now Pat. No. 6,206,888, which is a continuation-in-part of application No. 09/204,644, filed on Dec. 2, 1998, now abandoned, which is a continuation of application No. 08/947,619, filed on Oct. 9, 1997, now abandoned, which is a continuation-in-part of application No. 08/941,978, filed on Oct. 1, 1997, now abandoned.

(51) Int. Cl.[7] .................................................. A61F 11/00
(52) U.S. Cl. ....................................................... 606/108
(58) Field of Search .............................. 623/1.12, 1.23, 623/1.11; 606/108, 195

(56) References Cited

U.S. PATENT DOCUMENTS

| 5,534,007 A | * | 7/1996 | St. Germain et al. ....... 606/108 |
| 5,846,247 A | | 12/1998 | Unsworth et al. ........... 606/108 |
| 6,113,608 A | * | 9/2000 | Monroe et al. .............. 606/108 |
| 6,123,720 A | * | 9/2000 | Anderson et al. ............... 632/1 |

FOREIGN PATENT DOCUMENTS

| DE | 198 19 634 A1 | 11/1999 |
| DE | 198 38 414 A1 | 3/2000 |
| WO | 00/12031 | 3/2000 |

* cited by examiner

Primary Examiner—David O. Reip
Assistant Examiner—D. Jacob Davis
(74) Attorney, Agent, or Firm—Vidas, Arrett & Steinkraus, P.A.

(57) ABSTRACT

The inventive stent delivery system includes a catheter having a retractable outer sheath near its distal end. A shape memory contraction member having a memorized contracted shape is connected to the retractable outer sheath. A heat generating device connected to the shape memory contraction member causes the shape memory contraction member to heat up to its transition temperature and assume its contracted position, retracting the retractable outer sheath. Another embodiment utilizes 2 springs, a "normal" spring and a shape memory alloy (SMA) spring, the two springs selected and designed so that the "normal" has an expansion force which is less than SMA spring when the SMA spring is austenitic, but greater than the SMA spring when the SMA spring is martensitic. Yet another embodiment utilizes a shape memory latch which in its martensitic state abuts a stop to prevent a spring from moving the sheath proximally, but in its austenitic state releases the stop, allowing the spring to retract the sheath to release the stent for deployment.

6 Claims, 3 Drawing Sheets

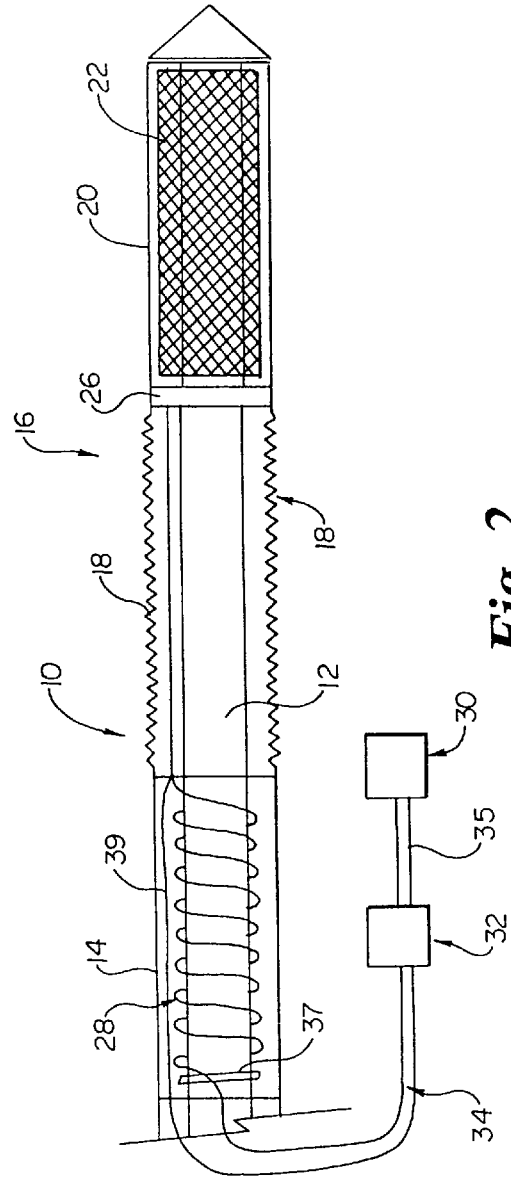
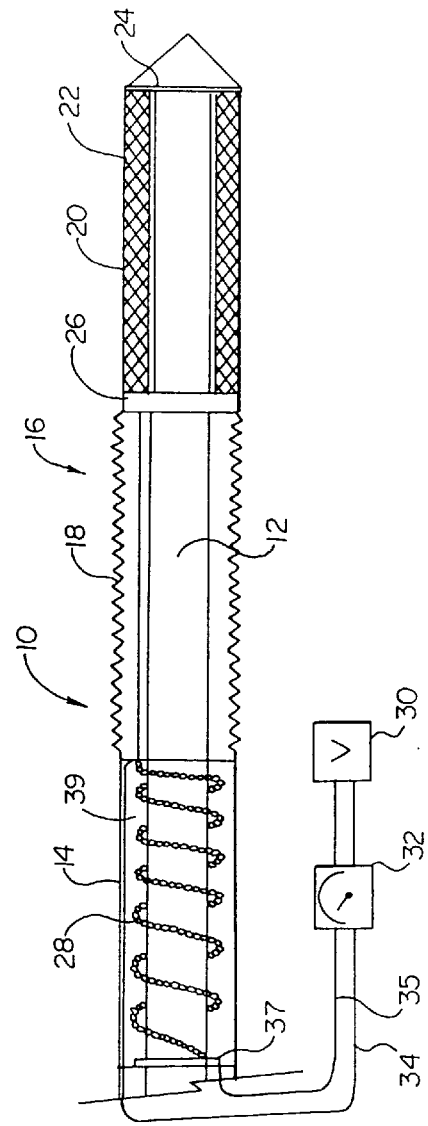

STENT DELIVERY SYSTEM USING SHAPE MEMORY RETRACTION

CROSS-REFERENCE TO RELATED APPLICATIONS

This application is a divisional application from application Ser. No. 09/283,444 filed on Apr. 1, 1999 now U.S. Pat. No. 6,206,888, which is a continuation-in-part of U.S. application Ser. No. 09/204,644, filed Dec. 2, 1998 now ABN, which is a continuation of U.S. application Ser. No. 08/947,619, filed Oct. 9, 1997 now ABN, which is a continuation-in-part of U.S. application Ser. No. 08/941,978, filed Oct. 1, 1997 now ABN, the entire contents of each of which are incorporated herein by reference.

BACKGROUND OF THE INVENTION

The present invention relates to an improved wire pull back delivery system. More specifically, the invention relates to a wire pull-back stent delivery system which utilizes a shape memory contraction member to retract the retractable outer sheath and deploy a medical implant for a minimally invasive application, such as an endovascular stent graft, vena cava filter, aneurysm repair particles, self-expanding stent, balloon expandable stent, or the like.

Delivery systems for deploying medical implants, such as an endovascular stent graft, vena cava filter, self-expanding stent, balloon expandable stent or the like, are a highly developed and well known field of medical technology. These medical devices have many well known uses and applications. In particular, a stent is a prosthesis which is generally tubular and which is expanded radially in a vessel or lumen to maintain its patency. Stents are widely used in body vessels, body canals, ducts or other body lumens. Balloon expandable stents are mounted on a balloon which when expanded delivers the stent, exerting radial force on the constricted portion of the body lumen to re-establish patency. A self-expanding stent is a stent which expands from a compressed delivery position to its original diameter when released from the delivery device, exerting radial force on the constricted portion of the body lumen to re-establish patency. One common self-expanding stent is manufactured of Nitinol, a nickel-titanium shape memory alloy, which can be formed and annealed, deformed at a low temperature, and recalled to its original shape with heating, such as when deployed at body temperature in the body. A common material for balloon expandable stents is stainless steel.

Wire pull-back stent delivery systems commonly assigned with this application include U.S. Pat. No. 5,571,135, U.S. Ser. No. 08/753,641 filed Sep. 27, 1996 and U.S. Pat. No. 5,733,267, the entire contents of which are hereby incorporated by reference. Another wire pull-back stent delivery system is shown in U.S. Pat. No. 5,360,401. One important factor in delivering the stent is a controlled precise retraction of the retractable outer sheath. What is needed is a wire pull-back stent delivery system which provides for a controlled and precise retraction of the retractable outer sheath and enables the physician to accurately determine proper positioning of the stent.

SUMMARY OF THE INVENTION

The inventive stent delivery system includes a catheter having a retractable outer sheath near its distal end. A shape memory contraction member having a memorized contracted shape is connected to the retractable outer sheath. A heat generating device connected to the shape memory contraction member causes the shape memory contraction member to heat up to its transition temperature and assume its contracted position, retracting the retractable outer sheath.

Another embodiment utilizes 2 springs, a "normal" spring and a shape memory alloy (SMA) spring, the two springs selected and designed so that the "normal" spring has an expansion force which is less than SMA spring when the SMA spring is austenitic, but greater than the SMA spring when the SMA spring is martensitic.

Yet another embodiment utilizes a shape memory latch which in its martensitic state abuts a stop to prevent a spring from moving the sheath proximally, but in its austenitic state releases the stop, allowing the spring to retract the sheath to release the stent for deployment.

BRIEF DESCRIPTION OF THE FIGURES

FIG. 1 shows a cross-sectional view of a first embodiment of the inventive catheter with a single coiled wire for its shape memory contraction member;

FIG. 2 shows a cross-sectional view of a second embodiment of the inventive catheter with a balloon beneath the stent and with a coil and/or twisted wire contraction member;

DESCRIPTION OF THE PREFERRED EMBODIMENTS

Figure 3:
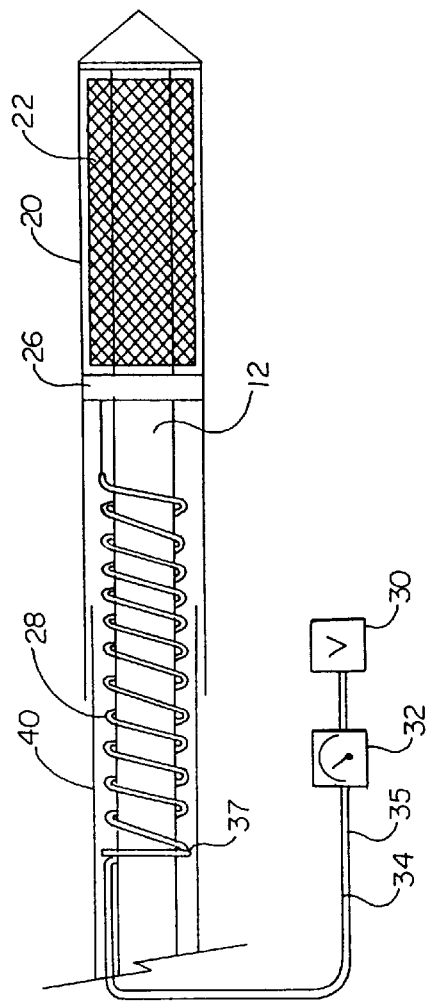
FIG. 3 shows a cross-sectional view of a third embodiment of the inventive catheter with a multiple wire contraction member with the wires coiled in parallel.

Referring to FIG. 1, the inventive catheter is shown generally at 10 and is of well known construction with an inner shaft 12 and an outer shaft 14. Connected to the outer shaft 14 is a retraction assembly shown generally at 16, which is comprised of a collapsible accordian section 18 and a stent sheath section 20. For more information on the collapsible retractable sheath please refer to U.S. Pat. No. 5,534,007 and PCT/US96/07143 filed May 17, 1996, both of which are commonly owned with this application and the entire contents of which are hereby incorporated by reference.

A medical device such as stent 22 is carried on inner shaft 12 under retraction assembly 16, as is well known in the art. Stent 22 can be self-expanding or balloon expandable. The inventive catheter may be used to delivery endovascular stent grafts, vena cava filters, aneurysm repair particles, self-expanding stents, balloon expandable stents, or the like.

An annular collar 26 is attached to the proximal portion of stent sheath 20 and a shape memory contraction member 28 is connected to annular collar 26. In this embodiment the shape memory contraction member 28 is a one-way Nitinol coiled wire spring, which after martensitic to austenitic transition has a shortened longitudinal length, causing annular collar 26 to be retracted proximally, collapsing accordian section 18 of the retractable outer sheath 16 and retracting stent sheath 20 so the medical device such as stent 22 can be delivered.

As is well known in the art Nitinol can be made with an austenitic final ($A_f$) temperature above body temperature. At room temperature the Nitinol wire is in its martensite phase and can be easily deformed. In the first embodiment the contraction member 28 is made from Nitinol wire, formed into a coil and heat set into a spring shape. After the spring is made, the spring is deformed at room temperature to elongate the spring. One end of the spring is attached to the annular collar 26 and the other end is fixedly attached to the inner shaft 12, at bumper 37.

In the first embodiment the shape memory contraction member 28 takes the form of a spring, however it should be understood that any geometry which resulted in a reduced longitudinal length, causing retraction could be utilized. The length of the spring would determine the amount of retraction and can be selected for various size stents. An alternate embodiment is an elongate Nitinol wire which shortens up longitudinally upon transition (muscle wire). With a one meter long wire which contracts 8% for example, a retraction of 80 mm could be provided, which is adequate for the various stent lengths in common use. Other shape memory alloys can provide various longitudinal contraction as a percent of length and could be utilized as well, if desired. Contraction member 28 could also take a zig-zag shape. The single wire 28 could also be replaced with a plurality of smaller diameter wires which could be braided, intertwined or the like, discussed below in more detail in connection with FIGS. 2 and 3.

Power supply 30 supplies power to rheostat 32 which supplies current to the Nitinol spring 28 via lead wire 34. The Nitinol spring 28 acts as a resistor and heats up, which causes the Nitinol to go through its transition temperature and assume its memorized shape. The transition temperature must be above body temperature. When the current flow is stopped, the spring 28 will stop contracting. Depending on the medium surrounding the spring 28 heat loss will vary and hence the time to stop contraction will vary as well. By replacing a manually operated pull wire with the inventive shape memory contraction member greater control of the retraction is achieved by using the rheostat to control the electrical input into the system. This will eliminate the jerking which can result from manual retraction of a pull wire, which can be caused by excessive force being used to overcome the high frictional and compressive forces created with larger stents.

Positive lead wire 34 is connected to contraction member 28 through contraction chamber 39. The negative lead wire is shown at 35. Contraction member 28 extends through contraction chamber 39 and is attached to annular collar 26. To protect the body from electrical and thermal conduction, either the contraction member 28 or contraction chamber 39 or both may be thermally and/or electrically insulated.

Although in the first embodiment the section of the contraction member 28 between contraction chamber 39 and annular collar 26 is Nitinol, contraction member 28 could be made of a different material such as stainless steel if desired. The geometry of the spring coil provides the contraction which retracts the outer sheath 16, so only the portions of contraction member 28 in the contraction chamber 39 needs to be manufactured of shape memory alloy.

Referring now to FIG. 2, stent 22 is shown with balloon 24 beneath it for dilation of a balloon expandable stent. Stent sheath 20 acts as a protective sheath for the stent and is withdrawn using shape memory actuator 28. The actuator or contraction member 28 is shown as multiple wires twisted and/or braided together.

Referring now to FIG. 3, a third preferred embodiment of the inventive catheter is shown in which actuator 28 is comprised of multiple wires coiled in parallel. If the wires are insulated, the distal ends of the wires can be connected and the wire leads are then both at the proximal end of the contraction member 28. Using smaller wires coiled in parallel enables the profile of the actuator 28 to be reduced while maintaining the ability to generate the same retraction force as a single larger wire. In this embodiment the accordian section 18 is replaced with a sliding sleeve design where stent sheath 20 moves proximally over the contraction chamber lumen 40 during retraction of stent sheath 20 to expose stent 22. The sliding sleeve section could also be designed to slid under lumen 40 if desired.

Figure 4:
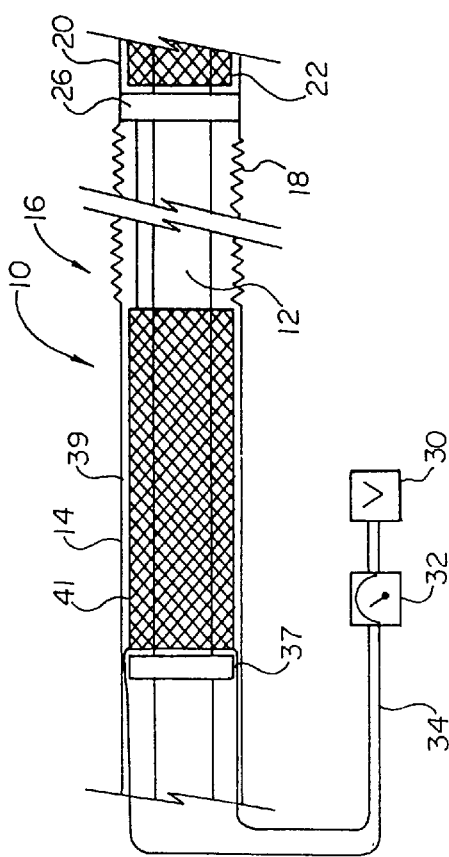
FIG. 4 shows a cross-sectional view of a fourth embodiment of the inventive catheter with a braided wire tube contraction member.

Referring now to FIG. 4, a fourth embodiment of the inventive catheter is shown in which the contraction member 41 is a shape memory braided wire tube. Shape memory contraction member 41 is connected to stent sheath 20 via annular collar 26. Upon heating, shape memory contraction member 41, moves proximally, hence moving stent sheath 20 proximally.

It should be understood from the above description of the different embodiments that the contraction member may consist of single wires, parallel wires, braided wires, twisted wires, or combinations thereof shaped into a coil. Also, the contraction member could consist of a braided tube comprised of single wires, parallel wires, braided wires, twisted wires, or combinations thereof.

It should also be understood that contraction member 28 or 41 could be heated using current, as in FIGS. 1–4, or could be heated conductively, either by being conductively connected to a heat source or by being bathed in a warm fluid bath.

It should also be understood that the shape memory contraction member 28 or 41 could be manufactured of one-way or two-way shape memory alloy. As is well known in the art two-way shape memory alloy takes two different shapes with different temperatures. Therefore, with two-way shape memory alloy contraction member 28 could contract at a first temperature selected during manufacture and expand at a second selected temperature. This would allow the retractable outer sheath 16 to be closed if the user changed their mind about delivery or during delivery.

The inventive device can deliver other medical devices other than stents and can be used in connection with fixed wire, single operator exchange (SOE)/rapid exchange (RX) or over the wire (OTW) catheter configurations.

Figure 5:
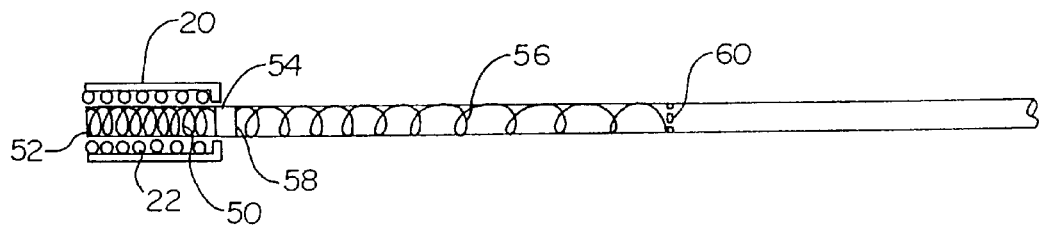
FIG. 5 shows a schematic cross-sectional view of a fifth embodiment of a shape memory retraction catheter, shown in the undeployed position.
Figure 6:
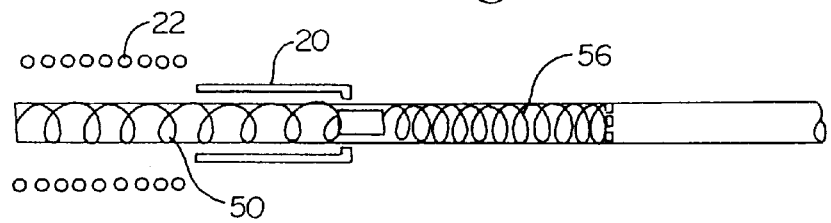
FIG. 6 shows a schematic cross-sectional view of a fifth embodiment of a shape memory retraction catheter, shown in the deployed position.

A fifth embodiment of a shape memory retraction catheter is shown in FIGS. 5 and 6, which shows a schematic view of a distal end of a catheter in both an undeployed and deployed position, shown respectively in FIGS. 5 and 6. In this embodiment a shape memory alloy retraction device is utilized to retract sheath 20 to release stent 22 for deployment. The shape memory alloy retraction device consists of first compressed spring 50, which is fixedly attached to the distal end of the catheter at 52 and is attached to the annular at 54, and second spring 56 which is attached to the annular collar at 58 and fixedly attached to the catheter at 60. Second compressed spring 56 is made of a shape memory alloy (SMA) which is formulated to be austenite at body temperature, which is approximately 37° C., and is designed to exert a distal force which is greater than the proximal force of first spring 50 at body temperature. First spring 50 is not made of shape memory alloy in the preferred embodiment, but could be made of SMA with a very low $A_f$ temperature, so that it did not change states with the cold water flush. Cold water flushing causes second spring 56 to transform to a martensite state, in which the proximal force exerted by spring 50, which is not affected by the cold water flushing, is greater than the distal force of second spring 56. The greater force exerted by spring 50 when spring 56 is martensitic moves the sheath 20 proximally to release the stent 22 for deployment. Although cold water flushing is preferred, it should be understood that any known medium cooling device could be utilized to cause second spring 50 to transform. With suitable design changes and if desired, second spring 56 could be heat actuated, if the transformation temperature is above body temperature.

An important feature of the fifth embodiment is that springs 50 and 56 are designed so that spring 50 has a proximal force which is less than the distal force of second spring 56 when spring 56 is austenitic, but greater than the distal force of spring 56 when spring 56 is martensitic. However, it should be understood that the positions of first spring 50 and second spring 56 could be switched and by suitable and opposite selection and design, second spring 56 could exert a proximal force on the sheath 20 which is less than the distal force exerted on the sheath 20 by the first spring 50, when the second spring 56 is in its martensitic state. However, when spring 56 is in its austenitic state it could be selected and designed to exert a proximal force on sheath 20 which is greater than the distal force exerted on the sheath 20 by the first spring 50.

An alternate embodiment for the device of FIGS. 5 and 6 would be to make both spring 50 and spring 56 of nitinol with equal $A_f > 37°$ C. (i.e. martensite at body temperature). With each of spring 50 and 56 connected to its own separate electric resistance heating (not shown), sheath 20 could be cycled back and forth as alternate springs 50 and 56 change from martensite to austenite by resistance heating.

Figure 7:
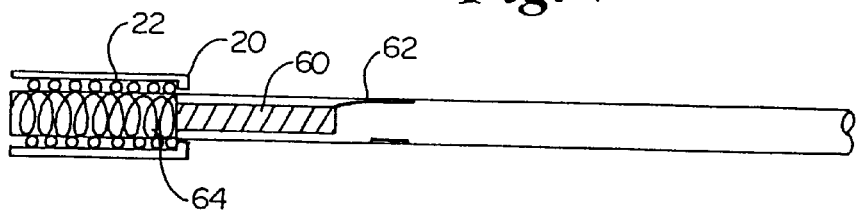
FIG. 7 shows a schematic cross-sectional view of a sixth embodiment of a shape memory retraction catheter, showing in the undeployed position.
Figure 8:
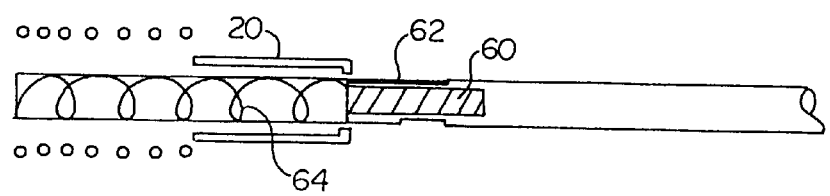
FIG. 8 shows a schematic cross-sectional view of a sixth embodiment of a shape memory retraction catheter, shown in the deployed position.

A sixth embodiment of a shape memory retraction catheter is shown in FIGS. 7 and 8, which shows a schematic view of a distal end of a catheter in both an undeployed and deployed position, shown respectively in FIGS. 7 and 8. In this embodiment the retractable sheath 20 includes a stop 60 extending from the proximal end of sheath 20. Stop 60 is engaged by a shape memory latch 62, which is fixedly attached to the catheter. A compressed spring 64 is arranged to exert a proximal force on sheath 20, which is held in the undeployed state by shape memory latch 62 as shown in FIG. 7. In FIG. 8, latch 62 is shown in a released position, which allows spring 64 to move sheath 20 proximally to release the stent 22 for deployment. Latch 62 may be actuated by either cooling or heating as discussed above, with suitable material selection. It should also be understood that latch 62 could be designed to soften to permit retraction.

Figure 9:
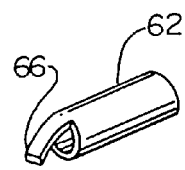
FIG. 9 shows the shape memory latch of the sixth embodiment in its martensitic state.
Figure 10:
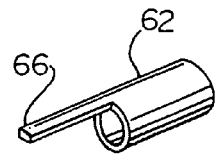
FIG. 10 shows the shape memory latch of the sixth embodiment in its austenitic state.

The shape memory latch 62 is shown in both its engaged and released states in FIGS. 9 and 10, respectively. As seen in FIG. 9, when the latch tip 66 is in its martensitic state, it angles downwardly to abut stop 60. As seen in FIG. 10, when the latch tip 66 is in its austenitic state, it straightens to release stop 60, allowing spring 64 to move sheath 20 proximally.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A catheter comprising:
   a catheter body having proximal and distal ends and including a retractable outer sheath near the distal end of the catheter body;
   a shape memory retraction device having a first state above a predetermined temperature and a second state below the predetermined temperature, the shape memory retraction device operatively connected to the retractable outer sheath and being constructed and arranged so that in the first state the retractable outer sheath is in an undeployed state and in the second state the retractable outer sheath is in a deployed state.

2. The catheter of claim 1 wherein the first state of the shape memory retraction device is austenitic.

3. The catheter of claim 2 wherein the shape memory retraction device comprises a first "normal" spring portion connected to the retractable outer sheath to provide a proximal retraction force, and a second shape memory alloy spring portion connected to the retractable outer sheath to provide a distal opposing force, the first and second spring portions being selected and designed so that the proximal retraction force is less than the distal opposing force when the second shape memory alloy spring portion is in its austenitic state, but where the proximal retraction force is greater than the distal opposing force when the second shape memory alloy spring portion is in its martensitic state.

4. The catheter of claim 1 wherein the shape memory retraction device is comprised of a spring connected to the retractable outer sheath to provide a proximal retraction force and a second shape memory device connected to the catheter body and having first and second states, the second shape memory device in its first state being operatively connected to the retractable outer sheath to prevent the retraction of the outer sheath, and in its second state releases the retractable outer sheath so that the spring may retract the sheath to its deployed state.

5. The catheter of claim 1 wherein the second shape memory device is comprised of a latch connected to the catheter body, the shape memory latch in its first state being operatively connected to the retractable outer sheath to prevent the retraction of the outer sheath, and in its second state releases the retractable outer sheath so that the spring may retract the sheath to its deployed state.

6. The catheter of claim 5 wherein the shape memory latch is softened in its second state to release the retractable outer sheath.

* * * * *